United States Patent [19]

Hofmeister et al.

[11] Patent Number: 4,567,002
[45] Date of Patent: Jan. 28, 1986

[54] PROCESS FOR THE PREPARATION OF 17-HALOETHYNYL STEROIDS, AND NOVEL 17-HALOETHYNYL STEROIDS

[75] Inventors: Helmut Hofmeister; Henry Laurent; Klaus Annen; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 603,855

[22] Filed: Apr. 25, 1984

[30] Foreign Application Priority Data

Apr. 25, 1983 [DE] Fed. Rep. of Germany ....... 3315324

[51] Int. Cl.$^4$ ................................................. C07J 5/00
[52] U.S. Cl. ............................. 260/397.4; 260/397.45
[58] Field of Search ..................... 424/243; 260/397.4, 260/397.45

[56] References Cited

U.S. PATENT DOCUMENTS 3,067,214 12/1962 Oberster .......................... 260/239.57
3,211,725 10/1965 Oberster et al. ................ 260/239.55
4,102,908 7/1978 Hofmeister et al. .............. 260/397.4

FOREIGN PATENT DOCUMENTS 1043675 9/1966 United Kingdom ............. 260/397.4

OTHER PUBLICATIONS

Tetrahedron, Band 22, Nr. 8, Aug. 1966, Seiten 2829–2836, Pergamon Press, Oxford, GB; C. Burgess et al.; "Modified Steroid Hormones–XLVI, Some 17alpha-ethynyl and 17alpha-Vinyl Derivatives", Seiten 2830, 2836.

*Primary Examiner*—Elbert L. Roberts
*Attorney, Agent, or Firm*—Millen & White

[57] ABSTRACT

17-haloethynyl steroids of the partial formula

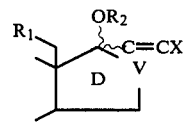

wherein
$R_1$ is hydrogen or methyl,
$R_2$ is alkyl of 1–4 carbon atoms, acyl of 1–7 carbon atoms, trimethylsilyl, 2-tetrahydropyranyl, or nitrate,
X is bromine or iodine, and
V is methylene, ethylene, vinylene, ethylidene, vinylidene or cyclopropylene, can be prepared by treating an ethynyl steroid of the partial formula

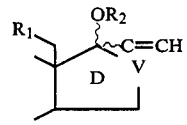

wherein $R_1$, $R_2$, and V are as defined above, in an inert solvent with a brominating agent or an iodinating agent in the presence of a silver salt. Certain new compounds are also provided.

11 Claims, No Drawings

PROCESS FOR THE PREPARATION OF 17-HALOETHYNYL STEROIDS, AND NOVEL 17-HALOETHYNYL STEROIDS

CROSS-REFERENCE TO RELATED APPLICATION

This application is related to U.S. patent application Ser. No. 552,537 of Nov. 16, 1983, whose disclosure is incorporated by reference herein.

This invention relates to a process for preparing 17-haloethynyl steroids and to new 17-haloethynyl steroids and their use.

SUMMARY OF THE INVENTION

It is an object of this invention to provide such a new process, products and uses thereof.

Upon further study of the specification and appended claims, further objects and advantages of this invention will become apparent to those skilled in the art.

These objects have been attained by providing a process for the preparation of 17-haloethynyl steroids of the partial formula

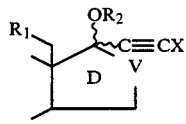

wherein
  $R_1$ is hydrogen or methyl,
  $R_2$ is alkyl of 1–4 carbon atoms, an acyl residue of 1–7 carbon atoms, trimethylsilyl, 2-tetrahydropyranyl, or nitrate,
  X is bromine or iodine, and
  V is methylene (—CH$_2$—), ethylene (—CH$_2$CH$_2$—), ethylidene (—CH(CH$_3$)—), vinylene (—CH=CH—), vinylidene (>C=CH$_2$(, or cyclopropylene

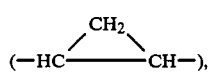

comprising treating an ethynyl steroid of the partial formula

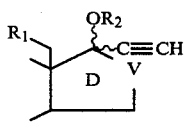

wherein $R_1$, $R_2$, and V are as defined above, in an inert solvent with a brominating agent or an iodinating agent, in the presence of a silver salt;

by providing 17-haloethynyl steroids fo Formula I or II

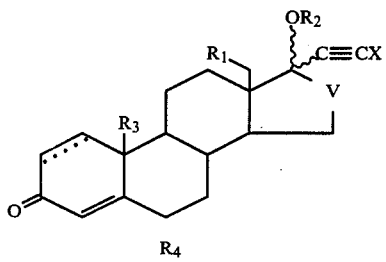

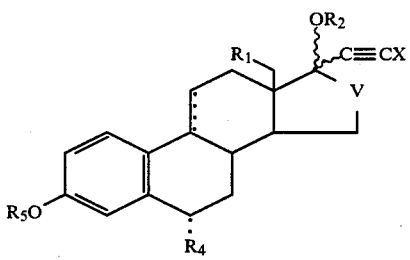

wherein
  $R_1$, $R_2$, X, and V are as defined above,
  ........ means single bonds or double bonds,
  $R_3$ is hydrogen or methyl,
  $R_4$ is hydrogen, methyl, or fluorine, and
  $R_5$ is hydrogen or alkyl of 1-4 carbon atoms; and
by providing a use of the 17-haloethynyl steroids of Formula I wherein $R_2$ is nitrate, for the preparation of pregnane derivatives of Formula III

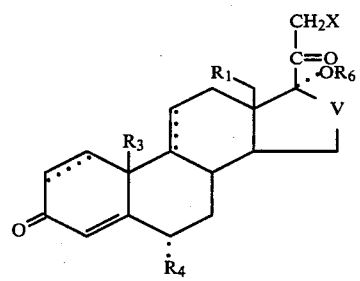

wherein
  $R_1$, $R_3$, $R_4$, X, and V are as defined above and
  $R_6$ is hydrogen or acyl of up to 7 carbon atoms.

DETAILED DISCUSSION

The process of this invention is conducted using a silver salt as the catalyst, e.g., in an amount of 1/1000 to 1, preferably 1/100 to 1/10 molar equivalent, based on the amount of the starting steroid. Suitable silver salts include, for example, silver nitrate, silver perchlorate, silver acetate, silver trifluoroacetate, silver fluoride, or silver sulfate. In general, the anion of the silver salt is not critical as long as it is reaction compatible. Of course, it is also required that the silver salt be sufficiently soluble or dispersible in the solvent to provide the amount of silver cations needed.

Suitable brominating or iodinating agents, are agents yielding bromine cations or iodine cations. These are generally conventional. Suitable for bromination are N-bromosuccinimide, N-bromoacetamide, N-bromophthalimide, N-bromo-p-toluenesulfamide, N-bromo-p-toluenesulfimide, N-bromocaprolactam, sodium hypobromide, and 1,3-dibromo-5,5-dimethylhydantoin. N- bromosuccinimide is especially suitable. N-iodosuccinimide is preferred as the iodinating agent.

The halogenating agent is preferably utilized in an equimolar quantity based on the amount of starting steroid, but an excess can also be used.

Suitable solvents include all those having inert behavior with respect to the halogenating agent, the silver salt and the reaction in general. In particular, suitable solvents include ketones, e.g., acetone, cyclohexanone, methyl ethyl ketone, and methyl isobutyl ketone, cyclic ethers, e.g., tetrahydrofuran and dioxane, aliphatic polyethers, such as ehtylene glycol dimethyl ether and diethylene glycol dimethyl ether, aromatic hydrocarbons, such as benzene or toluene, aliphatic alcohols, such as methanol, ethanol, and propanol, and solvents such as dimethylformamide, dimethylacetamide, hexamethylphosphoric triamide, and N-methylpyrrolidone, and the like.

The solvents can be utilized individually to dissolve or form a suspension of the starting steroid, or can be used as a mixture with one another. Typically, the solvent constitutes 70-99 weight % of the reaction mixture.

The 17-ethynyl-17$\beta$-OR$_2$ steroid used as the starting material can be substituted conventionally. The steroid can belong to the androstane or estrane series. The A, B, C, and D rings in the steroid molecule can contain usually at least one isolated double bond, such as those in the 4-, 5-, 5(10)-, 6-, 8-, 9(11)-, 11-, and/or 15-positions, and aromatic double bonds in the 1,3,5(10)-position. $C_{1-4}$-alkyl or $C_{2-4}$-alkenyl groups, such as methyl, ethyl or methylene, can be present, for example, in the 1-, 6-, or 11-position. $C_{1-4}$-alkoxy groups such as methoxy or ethoxy can be present, for example, in the 3-position if the A ring of the starting compound is aromatic. 3-keto and 3-OH groups are also included. Structures of typical androstanes and estranes which can be used include those disclosed in U.S. Pat. Nos. 4,119,626; 3,959,322; 3,927,046; and 4,081,537, whose disclosures are incorporated by reference herein. In general, substituents and other structural features are employable as long as they are reaction compatible.

The reaction of this invention can be conducted in the temperature range from 0° to 50° C. and is preferably carried out at room temperature. The reaction is usually completed, depending on the solvent employed, from 10 minutes up to 20 hours, which can be determined, for instance, by thin-layer chromatography.

After the reaction is terminated, the reaction mixture is worked up as usual, for example by precipitation, washing, extraction, recrystallization and/or column chromatography.

The compounds producible according to this invention include known compounds of known uses and novel compounds, all of which have an activity profile, e.g., pharmacological activity which is the same as that of the corresponding starting compounds without a 17-halo group. See, e.g., the references disclosed above. Many of the compounds can be used as intermediates for the preparation of known corticoids, such as the corresponding hydrocortisone derivatives.

Heretofore, 3-keto-$\Delta^4$-steroids with a 17-bromoethynyl- or 17-iodoethynyl-17-OR$_2$ system have been unknown, e.g., compounds of Formula (I). In the ethynylestradiol series, e.g., of Formula (II), the 17-bromo- and 17-iodoethynyl derivatives of 3,17$\beta$-dimethoxyethynylestradiol have been disclosed but are prepared in a cumbersome procedure by reacting the corresponding lithiumethynyl steroid with bromotrifluoromethane and with heptafluoro1-iodopropane, respectively (C. Burges et al., Tetrahedron 23 : 4111 [1967]). 17-bromoethynyl-3,17$\beta$-dipyranyloxy-1,3,5(10)-estratriene has been mentioned in U.S. Pat. No. 3,256,273.

Preferred process products of the method of this invention are the 17-haloethynyl steroids of Formulae (I) and (II) exhibiting the same pharmacological activity spectrum as the structurally analogous 17-ethynyl steroids, e.g., the compounds of Formula I are all useful as progestational agents and the compounds of Formula II are all useful as estrogenic agents. They are also valuable intermediates for the production of other pharmacologically effective steroids, for example those described in European Patent Application No. 83109753.0, whose disclosure is incorporated by reference herein, e.g., using fully conventional methods.

Especially valuable products of the process are those of Formula I and especially those in which $R_1$ is hydrogen and/or $R_2$ is a nitrate ester and/or $R_3$ is methyl. In particular, the nitrate esters of these 17-haloethynyl steroids are valuable intermediates for the preparation of pregnane derivatives of general Formula III.

All of the compounds of this invention and all of the products producible by the process of this invention can also be used to prepare other compounds of this invention and/or other products producible by the process of this invention, using fully conventional reactions.

Formula III compounds can be prepared, for example, under the conditions described in U.S. Pat. No. 4,102,908 whose disclosure is incorporated by reference herein. Surprisingly, in this reaction, one of the aforementioned silver salts can be utilized as the catalyst with an even greater success than attainable with conventional agents, e.g., mercury salts. An additional advantage is that the use of silver salts results in less pollution of the environment. The amounts and types of silver salts and their general use are as described above. Preferred lower carboxylic acids for use in this reaction are formic acid or acetic acid. Generally, alkane carboxylic acids of up to 7-C atoms can be used as cocatalyst. The reaction is preferably conducted in a dipolar aprotic or basic solvent usually constituting about 70-99 weight % of the reaction medium. Examples of dipolar aprotic solvents include hexamethylphosphoric triamide, N-methylpyrrolidone, dimethylformamide, dimethyl acetamide, dimethyl sulfoxide, sulfolane, etc. Examples of basic solvents include pyridine, toluidine, triethylamide, etc. The process of this invention is suitably carried out at room temperature. However, the reaction can also be readily accomplished at a lower or at an elevated temperature in the range, e.g., from −10° to 80° C. Preferably, 0.01-0.1 mole of silver salt per mole of steroid to be reacted is utilized as the catalyst. The amount of carboxylic acid is a conventional amount with respect to the amount of starting material steroid.

In the foregoing acyl is preferably alkanoyl. Suitable alkyl groups and alkyl moieties include methyl, ethyl, n-propyl, isopropyl, n-butyl, isobutyl, secbutyl, t-butyl, pentyl, hexyl, heptyl, etc.

The compounds of this invention and the products producible by the process of this invention can be used for the mentioned purposes in mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react wtih the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrum, exlixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

Dosages and regimens of administration are fully analogous to the conventional analogous agents mentioned above for each of the mentioned uses. Typically, the unit dosage for progestational or estrogenic use is 0.01–0.5 mg and the daily dosage for human beings, respectively, is 0.05–0.5 mg and 0.01–10 mg.

The chemical reactions described above are generally disclosed in terms of their broadest application to the preparation of the various compounds. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Many of the starting materials for the process of this invention are known; see, e.g., the foregoing references. Those which are new can be prepared conventionally in analogy to the preparation of the known compounds, e.g., from the corresponding free 17-ethynyl-17-hydroxy steroids as follows:

Under agitation and after adding 5.0 g of 4-dimethylaminopyridine, 25 ml of benzoyl chloride is added dropwise at room temperature to 5.0 g of 17α-ethynyl-17β-hydroxy4-estren-3-one in 200 ml of pyridine. After 4 days, the pyridine is extensively removed by distillation, the residue is taken up in ethyl acetate, the solution is washed repeatedly with hydrochloric acid (1:1) to remove the pyridine, the solution is neutralized with sodium bicarbonate solution and dried over sodium sulfate. Chromatography of the crude product on silica gel with ethyl acetate/hexane yields 3.9 g of 17α-benzoyloxy-17β-ethynyl-4-estren-3-one, mp 243.3° C.; or 5.0 g of 17α-ethynyl-17β-hydroxy-4-estren-3-one is suspended in 50 ml of tetrahydrofuran and combined at room temperature with 5 ml of dihydropyran and 120 mg of p-toluene-sulfonic acid. After 20 hours, the reaction mixture is diluted with ethyl acetate, washed neutral, and the solution dried over sodium sulfate. After chromatography on silica gel with ethyl acetate/hexane, 4.5 g of 17α-ethynyl-17β-tetrahydropyranyloxy-4-estren-3-one is obtained, mp 135.1° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight. The yields indicated refer to percent of theory.

(A) EXAMPLES FOR THE PROCESS OF THIS INVENTION

EXAMPLE 1

At room temperature, 1.0 g of 17α-ethynyl-18-methyl-17β-trimethylsiloxy-4-estren-3-one in 30 ml of anhydrous acetone is combined with 550 mg of N-bromosuccinimide and 50 mg of silver nitrate. After 45 minutes, the reaction mixture is poured into ice/water. The thus-precipitated product is suctioned off, washed with water, dissolved in ethyl acetate, and dried over sodium sulfate. The crude product is recrystallized from acetone/hexane, thus obtaining 950 mg of 17α-bromoethynyl-18-methyl-17β-trimethylsiloxy-4-estren-3-one, mp 181.7° C.

Preparation of starting material:

At 0° C., 2.0 g of 17α-ethynyl-17β-hydroxy-18-methyl-4-estren-3-one in 40 ml of pyridine is combined with 10 ml of trimethylchlorosilane. After 1.5 hours, the solution is introduced into ice/water, the thus-precipitated product is filtered off, dissolved in ethyl acetate, and washed with water. Recrystallization of the crude product from acetone/hexane yields 0 1.6 g of 17α-ethynyl-18-methyl-17β-trimethylsiloxy-4-estren-3-one, mp 222.1° C.

EXAMPLE 2

At room temperature, 1.0 g of 17β-acetoxy-17αethynyl-3-methoxy-1,3,5(10)-estratriene is stirred in 30 ml of tetrahydrofuran with 700 mg of N-iodosuccinimide and 50 mg of silver nitrate for 45 minutes and worked up as indicated in Example 1. Recrystallization of the crude product from acetone/hexane yields 1.0 g of 17β-acetoxy-17α-iodoethynyl-3-methoxy-1,3,5(10)-estratriene, mp 150.5° C. (decomposition).

EXAMPLE 3

2.0 g of 17α-ethynyl-17β-nitrooxy-4-androsten-3-one in 40 ml of acetone is stirred for 90 minutes with 1.1 g of N-bromosuccinimide and 100 mg of silver nitrate. The reaction mixture is stirred into ice/water, the precipitated product is suctioned off, dissolved in ethyl acetate, washed with water, and dried, thus obtaining 1.8 g of 17α-bromoethynyl-17β-nitrooxy-4-androsten-3-one as a foam.

EXAMPLE 4

1.0 g of 17α-ethynyl-17β-trifluoroacetoxy-4-androsten-3-one in 30 ml of tetrahydrofuran is combined with 550 mg of N-bromosuccinimide and 50 mg of silver nitrate. After 60 minutes, the reaction mixture is worked up as described in Example 3, thus isolating 960 mg of 17α-bromoethynyl-17β-trifluoroacetoxy-4-androsten-3-one as a foam.

EXAMPLE 5

Analogously to Example 3, 1.8 g of 17α-ethynyl-17β-nitrooxy-4-estren-3-one is reacted with N-bromosuccinimide and silver nitrate, thus isolating 1.6 g of 17α-bromoethynyl-17β-nitrooxy-4-estren-3-one as a solid foam.

EXAMPLE 6

Analogously to Example 1, 17β-acetoxy-17α-ethynyl-4-estren-3-one is reacted, in the presence of silver nitrate as the catalyst, in tetrahydrofuran for 40 minutes with N-bromosuccinimide and worked up, thus obtaining, in an 87% yield, 17β-acetoxy-17α-bromoethynyl-4-estren-3-one, decomposition point 150.1° C.

EXAMPLE 7

Analogously to Example 1, 17β-acetoxy-17α-ethynyl-4-androsten-3-one is reacted in tetrahydrofuran with the use of silver nitrate as the catalyst with N-bromosuccinimide for 45 minutes and worked up, thus obtaining, in an 83% yield, 17β-acetoxy-17α-bromoethynyl-4-androsten-3-one, decomposition point 133.6° C.

EXAMPLE 8

Analogously to Example 1, 17β-acetoxy-17α-ethynyl-4-androsten-3-one is reacted in acetone with the use of silver trifluoroacetate as the catalyst for 60 minutes with 1,3-dibromo-5,5-dimethylhydantoin and worked up, thus producing, in a 76% yield, 17β-acetoxy-17α-bromoethynyl-4-androsten-3-one, decomposition point 130.0° C.

EXAMPLE 9

Analogously to Example 1, 17α-ethynyl-17β-trifluoroacetoxy-4-estren-3-one is reacted in acetone, using silver nitrate as the catalyst, for 90 minutes with N-bromosuccinimide and worked up, thus obtaining, in an 86% yield, 17α-bromoethynyl-17β-trifluoroacetoxy-4-estren-3-one as a foam.

EXAMPLE 10

Analogously to Example 1, 17β-benzoyloxy-17α-ethynyl-4-estren-3-one is reacted in toluene, using silver trifluoroacetate as the catalyst, for 20 hours with N-bromosuccinimide and worked up, thus obtaining, in a 68% yield, 17β-benzoyloxy-17α-bromoethynyl-4-estren-3-one, decomposition point 182.0° C.

EXAMPLE 11

Analogously to Example 1, 17α-ethynyl-17β-(2-tetrahydropyranyloxy)-4-estren-3-one is reacted in acetone with the use of silver nitrate as the catalyst for 60 minutes with N-bromosuccinimide and worked up, thus producing, in a 75% yield, 17α-bromoethynyl-17β-(2-tetrahydropyranyloxy)-4-estren-3-one, mp 115.5° C.

EXAMPLE 12

Analogously to Example 1, 17β-acetoxy-17α-ethynyl-4-estren-3-one is reacted in tetrahydrofuran, using silver nitrate, for 30 minutes with N-iodosuccinimide and worked up, thus producing, in an 81% yield, 17β-acetoxy-17α-iodoethynyl-4-estren-3-one, decomposition point 134.0° C.

EXAMPLE 13

Analogously to Example 1, 17β-acetoxy-17α-ethynyl-4-androsten-3-one is reacted in tetrahydrofuran, using silver nitrate as the catalyst, for 20 minutes with N-iodosuccinimide and worked up, thus obtaining, in a 77% yield, 17β-acetoxy-17α-iodoethynyl-4-androsten-3-one, decomposition point 157.0° C.

EXAMPLE 14

At room temperature, 8.5 g of N-bromosuccinimide and 500 mg of silver nitrate are added to 16.0 g of 17α-ethynyl-17β-nitrooxy-1,4-androstadien-3-one in 80 ml of 1-methyl-2-pyrrolidone. After 45 minutes, the reaction mixture is stirred into ice water. The thus-precipitated product is suctioned off, dissolved in ethyl acetate, washed with water, and dried, thus isolating 15.6 g of 17α-bromoethynyl-17β-nitrooxy-1,4-androstadien-3-one as a foam.

EXAMPLE 15

At room temperature 800 mg of 17β-ethynyl-17α-formyloxy-4-androsten-3-one in 8 ml of 1-methyl-2-pyrrolidone is combined with 500 mg of N-bromosuccinimide and 50 mg of silver nitrate. After 45 minutes, the reaction mixture is introduced into ice water, the thus-precipitated product is suctioned off, dissolved in ethyl acetate, washed with water, and dried over sodium sulfate, thus obtaining 890 mg of 17β-bromoethynyl-17α-formyloxy-4-androsten-3-one, mp 202.6° C.

EXAMPLE 16

(a) At −20° C., 5.4 ml of fuming nitric acid is added dropwise to 5.0 g of 17α-ethynyl-17β-hydroxy-4,9(11)-androstadien-3-one [J. Org. Chem. 44 : 1582 (1979)] in 50 ml of acetic anhydride. The reaction mixture is introduced into ice water, the precipitated product is suctioned off, dissolved in ethyl acetate, washed with water, and dried over sodium sulfate, thus obtaining 4.8 g of 17α-ethynyl17β-nitrooxy-4,9(11)-androstadien-3-one, mp 134.6° C. (decomposition).

(b) At room temperature, 4.0 g of 17α-ethynyl-17β-nitrooxy-4,9(11)-androstadien-3-one in 20 ml of 1-methyl-2-pyrrolidone is reacted with 2.3 g of N-bromosuccinimide and 150 mg of silver nitrate. After 30 minutes, the reaction mixture is introduced into ice water. The thus-precipitated product is suctioned off, dissolved in ethyl acetate, washed with water, and dried over sodium sulfate, thus isolating 4.0 g of 17α-bromoethynyl-17β-nitrooxy-4,9(11)-androstadien-3-one as a foam.

(B) EXAMPLES FOR USING THE PRODUCTS OF THE PROCESS

EXAMPLE 1

(a) At 0° C., 13.0 g of 17α-bromoethynyl-17β-nitrooxy-1,4-androstadien-3-one in 20 ml of 1-methyl-2-pyrrolidone is combined with 100 ml of concentrated formic acid, 500 mg of silver nitrate is added thereto, and the reaction mixture is stirred at room temperature.

After 6 hours, the reaction mixture is poured into ice water. The thus-precipitated product is suctioned off, dissolved in ethyl acetate, washed with water, and dried over sodium sulfate, thus obtaining 9.6 g of 21-bromo-17-formyloxy-1,4-pregnadiene3,20-dione, mp 191.7° C. (decomposition).

(b) Under argon, 4.0 g of 21-bromo-17-formyloxy-1,4-pregnadiene-3,20-dione is agitated in a mixture of 150 ml of methanol and 24 ml of water with 1.3 g of potassium bicarbonate at room temperature. After one hour, the reaction mixture is introduced into ice water, the precipitated product is suctioned off, dissolved in ethyl acetate, washed with water, and dried over sodium sulfate, yielding 3.2 g of 21-bromo-17-hydroxy-1,4-pregnadiene-3,20-dione, mp 189.9° C. (decomposition).

(c) 3.0 g of 21-bromo-17-hydroxy-1,4-pregnadiene-3,20-dione is stirred in 60 ml of acetone with 3.0 g of potassium acetate at 50° C. The reaction mixture is introduced into ice water after 2 hours, the thus-precipitated product is suctioned off, dissolved in ethyl acetate, washed with water, and dried over sodium sulfate, thus producing 2.6 g of 21-acetoxy-17-hydroxy-1,4-pregnadiene-3,20-dione, mp 214° C.

EXAMPLE 2

500 mg of 17β-bromoethynyl-17α-formyloxy-4-androsten-3-one is dissolved in 1 ml of 1-methyl-2-pyrrolidone and combined at 0° C. with 5 ml of concentrated formic acid. Then 50 mg of silver nitrate is added thereto at room temperature. After 2 hours, the reaction mixture is poured into ice water. The precipitated product is suctioned off, dissolved in ethyl acetate, washed with water, and dried over sodium sulfate, thus obtaining 380 mg of 21-bromo-17-formyloxy4-pregnene-3,20-dione, mp 192.0° C. (decomposition).

EXAMPLE 3

(a) 4.5 g of 17α-bromoethynyl-17β-nitrooxy-4,9(11)-androstadien-3-one is dissolved in 10 ml of 1-methyl-2-pyrrolidone. At 0° C., 50 ml of concentrated formic acid and 200 mg of silver nitrate are added thereto. The mixture is stirred at room temperature. After 8 hours, the reaction mixture is introduced into ice water. The precipitated product is suctioned off, dissolved in ethyl acetate, washed neutral with water, and dried over sodium sulfate, thus isolating 3.6 g of 21-bromo-17-formyloxy-4,9(11)-pregnadiene-3,20-dione, mp 195.3° C. (decomposition).

(b) 2.5 g of 21-bromo-17-formyloxy-4,9(11)-pregnadiene-3,20-dione is stirred at room temperature under argon in 100 ml of methanol and 18 ml of water with 1.3 g of potassium bicarbonate. After 45 minutes, the reaction mixture is introduced into ice water which contains sodium chloride, the thus-precipitated product is suctioned off, washed repeatedly with water, and dried under vacuum, thus obtaining 2.2 g of 21-bromo-17-hydroxy-4,9(11)-pregnadiene-3,20-dione [J. Org. Chem. 44 : 1582 (1979)]in the form of a crude product which is stirred in 50 ml of acetone and 2.7 g of potassium acetate at 50° C. After 2 hours, the reaction mixture is stirred into ice water, the thus-precipitated product is suctioned off, dissolved in ethyl acetate, washed with water, and dried over sodium sulfate, thus obtaining 1.9 g of 21-acetoxy-17-hydroxy-4,9(11)-pregnadiene-3,20-dione, mp 235.8° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 17-haloethynyl androstane or estrane of the partial formula

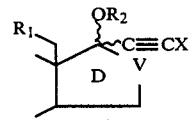

wherein
$R_1$ is hydrogen or methyl,
$R_2$ is alkyl of 1–4 carbon atoms, alkanoyl of 1–7 carbon atoms, trimethylsilyl, 2-tetrahydropyranyl, or nitrate,
X is bromine or iodine, and
V is methylene, ethylene, ethylidene, vinylene, vinylidene, or cyclopropylene,
comprising treating a corresponding ethynyl androstane or estrane of the partial formula

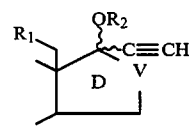

wherein $R_1$, $R_2$, and V are as defined above, in a reaction compatible solvent with an effective brominating agent or iodinating agent in the presence of a catalytically effective amount of silver cations.

2. A process of claim 1, wherein the amount of silver is 1/1000 to 1 molar equivalent based on the amount of starting steroid.

3. A process of claim 1, wherein the amount of silver is 1/100 to 1/10 molar equivalent based on the amount of starting steroid.

4. A process of claim 1, wherein the silver cations are added in the form of silver acetate, trifluoroacetate, nitrate, perchlorate, fluoride or sulfate.

5. A process of claim 1, wherein a brominating agent is used which is N-bromosuccinimide, N-bromoacetamide, N-bromophthalimide, N-bromo-p-toluenesulfamide, N-bromo-p-toluenesulfimide, N-bromocaprolactam, sodium hypobromide, or 1,3-dibromo-5,5-dimethylhydantoin.

6. A process of claim 1, wherein an iodinating agent is used which is N-iodosuccinimide.

7. A process of claim 1, wherein the solvent is a ketone, a cyclic ether, an aliphatic polyether, an aromatic hydrocarbon, an aliphatic alcohol, dimethylformamide, dimethylacetamide, hexamethylphosphoric triamide or N-methylpyrrolidone.

8. A process of claim 1, wherein the starting estrane or androstane has at least a double bond in the 4-, 5-, 5(10)-, 6-, 8-, 9(11)-, 11-, or 15-position; an aromatic unsaturation in the 1,3,5(10)-positions; a 1-, 6- or 11-$C_{1-4}$-alkyl or $C_{2-4}$-alkenyl group; a 3-$C_{1-4}$-alkoxy group; or a combination thereof.

9. A process of claim 1 which is carried out at 0°–50° C., for 10 minutes to 20 hours.

10. A process of claim 1, wherein the product steroid is of the formula

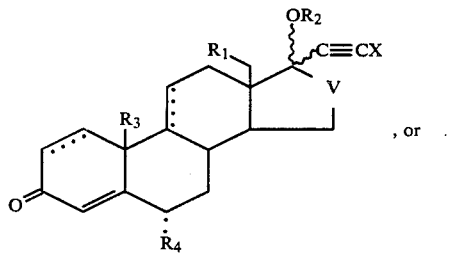

, or

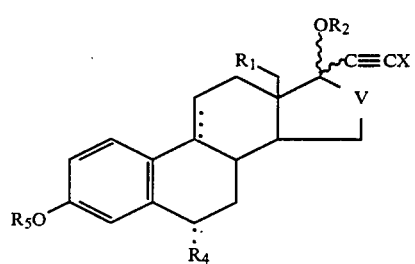

wherein $R_1$, $R_2$, X and V are as defined in claim 1,

........ is a single or double bond, $R_3$ is H or methyl, $R_4$ is H, methyl or fluorine, and $R_5$ is H, or $C_{1-4}$-alkyl.

11. A process for preparing a compound of the following formula,

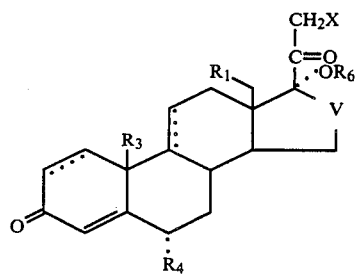

wherein $R_1$ is hydrogen or methyl, $R_3$ is hydrogen or methyl, $R_4$ is hydrogen, methyl or fluorine, X is bromine or iodine, V is methylene, ethylene, ethylidene, vinylene, vinylidene, or cyclopropylene, and $R_6$ is H or $C_{1-7}$ alkanoyl, comprising treating a corresponding compound of the formula

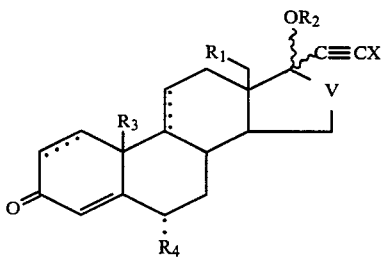

in the presence of a catalytically effective amount of silver cations and $C_{1-7}$ alkane carboxylic acid.

* * * * *